US00RE43989E

(19) United States
(12) Reissued Patent
Furukawa et al.

(10) Patent Number: US RE43,989 E
(45) Date of Reissued Patent: Feb. 12, 2013

(54) LOAD CELL ATTACHMENT STRUCTURE

(75) Inventors: Takashi Furukawa, Utsunomiya (JP); Naotaka Kumakiri, Utsunomiya (JP); Mikihito Kojima, Utsunomiya (JP); Masashi Yoshifuku, Utsunomiya (JP); Tatsuya Yamazaki, Dublin, OH (US); Toyohiko Shindo, Tochigi (JP); Harutomi Nishide, Utsunomiya (JP); Shigeru Endo, Tochigi (JP); Kenji Sato, Sakura (JP)

(73) Assignees: Honda Motor Co., Ltd., Tokyo (JP); TS Tech Co., Ltd., Asaka-shi (JP)

(21) Appl. No.: 12/784,111

(22) Filed: May 20, 2010

Related U.S. Patent Documents

Reissue of:
(64) Patent No.: 7,373,846
Issued: May 20, 2008
Appl. No.: 11/219,213
Filed: Sep. 2, 2005

(30) Foreign Application Priority Data

Sep. 7, 2004 (JP) ..... 2004-259502
Sep. 7, 2004 (JP) ..... 2004-259503

(51) Int. Cl.
*G01L 1/26* (2006.01)
*G01G 19/08* (2006.01)
*G01G 19/52* (2006.01)

(52) U.S. Cl. ..... 73/862.621; 73/862.622; 73/862.632; 177/136; 177/144; 177/187; 177/189

(58) Field of Classification Search ..... 73/862.621
See application file for complete search history.

(56) References Cited

U.S. PATENT DOCUMENTS

| | | | | |
|---|---|---|---|---|
| 4,106,370 | A * | 8/1978 | Kraus et al. | 73/761 |
| 4,302,136 | A * | 11/1981 | Abe et al. | 411/158 |
| 4,421,186 | A * | 12/1983 | Bradley | 177/139 |
| 5,837,946 | A * | 11/1998 | Johnson et al. | 177/136 |
| 6,161,891 | A | 12/2000 | Blakesley | |
| 6,323,443 | B1 * | 11/2001 | Aoki et al. | 177/144 |
| 6,401,855 | B1 * | 6/2002 | Wolfe | 180/271 |
| 6,748,814 | B2 * | 6/2004 | Ishida et al. | 73/862.391 |
| 9,616,997 | * | 7/2005 | Thakur et al. | 177/136 |
| 6,969,809 | B2 * | 11/2005 | Rainey | 177/136 |
| 2005/0284668 | A1 * | 12/2005 | Hida et al. | 177/136 |
| 2006/0010984 | A1 * | 1/2006 | Yamazaki | 73/761 |
| 2007/0057527 | A1 * | 3/2007 | Endo et al. | 296/65.13 |

FOREIGN PATENT DOCUMENTS

WO WO2004079308 * 9/2004

OTHER PUBLICATIONS

Abstract of JP2001187911.*
Abstract of JP9229036.*

* cited by examiner

*Primary Examiner* — Lisa Caputo
*Assistant Examiner* — Punam Roy
(74) *Attorney, Agent, or Firm* — Rankin, Hill & Clark LLP

(57) ABSTRACT

This load cell attachment structure includes a male screw which is formed on a load sensing part of the load cell, a nut which attaches the load cell to the attachment plate by engaging with the male screw, and a wave washer which is disposed between the attachment plate and the nut.

51 Claims, 5 Drawing Sheets

LOAD CELL ATTACHMENT STRUCTURE

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to a load cell attachment structure.

Priority is claimed on Japanese Patent Application No. 2004-259502, filed Sep. 7, 2004, and on Japanese Patent Application No. 2004-259503, filed Sep. 7, 2004, the content of which is incorporated herein by reference.

2. Description of Related Art

In order to control operating and the like of an air bag system when a collision of a vehicle happens, a load cell which measures load acting on a seat is mounted on the vehicle. Then, it is determined whether an occupant is seated or not, and whether the occupant who is seated is an adult or a child, and the like.

For example, there is a system which includes stud bolts projecting above, which is disposed on the front and rear of sliders of bilateral seat rails, a plate member which is fixed on the stud bolts and a seat frame. One end of the plate member is fixed on a tip of the stud bolts which go through holes of the seat frame, and the other end of the plate member is fixed on the seat frame (refer to U.S. Pat. No. 6,161,891). In the reference, amount of deformation of the plate member is measured.

Also, as shown in FIG. 7, there is a system in which a male screw 102 is disposed on a load sensing part 101 of a load cell 100, the load cell 100 is attached to a slider 103 of a seal rail facing upward toward the load sensing part 101, and an attachment plate 104 of a seat frame is attached to the load cell 100 by engaging a nut 105 with the male screw 102. In this system, when the attachment plate 104 is attached to the load sensing part 101 by fastening the nut 105 to the male screw 102 tightly, if only the attachment plate 104 of the seat frame warps or inclines slightly due to a minor accident of the vehicle or the like, the load cell 100 measures slight loads are caused by the warp or the incline. As a result, the load cell 100 cannot measure loads accurately. Accordingly, as shown in FIG. 8, it is proposed that clearance which allows warp or the incline of the attachment plate 104 be formed between the nut 105 and the load sensing part 101 by disposing a collar 106 between the nut 105 and the load sensing part 101. However, in this system, a fastening force along the longitudinal direction of the male screw 102 acts on the load sensing part 101 through the collar 106. As a result, the load cell 100 senses undesired load. In other words, drift force along the axis is caused on the load cell 100.

SUMMARY OF THE INVENTION

It is therefore an object of the invention to provide a load cell attachment structure capable of preventing a load cell from sensing undesired loads which are caused by warp or a incline of the attachment plate, and as a result, load cell can measure loads accurately.

A load cell attachment structure of the present invention for attaching a load cell to an attachment plate includes: a first fastening part which is formed on a [load sensing part] *main body* of the load cell; a second fastening part which attaches the load cell to the attachment plate by engaging with the first fastening part; and an elastic body which is disposed between the attachment plate and the second fastening part.

According to the present invention, since the elastic body is disposed between the attachment plate and the second fastening part, if the attachment plate warps or inclines, such wrap or incline is absorbed by deformation of the elastic body. Therefore, *a load sensing part of* the load cell does not sense an undesired load which is caused by the warp or the incline of the attachment plate. As a result, it is possible to measure loads which act on the load sensing part exactly.

It is preferable that the load cell attachment structure further include a washer part which covers the load sensing part, and is disposed between the load sensing part and the attachment plate, and a collar part which is disposed between the washer part and the second fastening part, wherein a length of the collar part along an axis thereof is longer than a thickness of the attachment plate.

According to the present invention, a clearance which absorbs the wrap or incline of the attachment plate is appropriately formed between the washer part and the second fastening part by the collar part. In addition, the fastening force which is introduced through the collar part is dispersed on the load sensing part evenly, by the washer part. Therefore, the load cell does not sense an undesired load which is caused by the warp or the incline of the attachment plate, and the fastening force. As a result, it is possible to measure loads which act on the load sensing part exactly.

It is preferable in the load cell attachment structure of the present invention, that the first fastening part be a male screw, the second fastening part be a nut, the elastic body be disposed between the attachment plate and the nut, and the collar part be disposed between the washer part and the nut. Alternatively, it is preferable in the load cell attachment structure of the present invention, that the first fastening part be a female screw, the second fastening part be a bolt, the elastic body be disposed between the attachment plate and a top of the bolt, and the collar part be disposed between the washer part and the top of the bolt.

It is preferable for the load cell attachment structure of the present invention that the collar part be formed as a single body with the washer part.

According to the present invention, since the collar part is formed as a single body with the washer part, it is possible to reduce quantity of parts and time in assembling.

A load cell attachment structure of the present invention for attaching a load cell to an attachment plate includes: a first fastening part which is formed on a [load sensing part] *main body* of the load cell; a second fastening part which attaches the load cell to the attachment plate by engaging with the first fastening part; a washer part which covers the load sensing part, and is disposed between the load sensing part and the attachment plate; and a collar part which is disposed between the washer part and the second fastening part, wherein a length of the collar part along an axis thereof is longer than a thickness of the attachment plate.

According to the present invention, a clearance which absorbs the wrap or incline of the attachment plate is appropriately formed between the washer part and the second fastening part by the collar part. In addition, the fastening force which is introduced through the collar part is dispersed on the load sensing part evenly by the washer part. Therefore, the load cell does not sense an undesired load which is caused by the warp or incline of the attachment plate, and dispersion of initial values of the load cell, which is caused by difference in fastening torque is not caused. As a result, it is possible to measure loads which act on the load sensing part exactly.

It is preferable in the load cell attachment structure of the present invention that the first fastening part be a male screw, the second fastening part be a nut, and the collar part be disposed between the washer part and the nut. Alternatively, it is preferable in the load cell attachment structure of the present invention, that the first fastening part be a female screw, the second fastening part be a bolt, and the collar part be disposed between the washer part and a top of the bolt.

It is preferable in the load cell attachment structure of the present invention that the collar part be formed as a single body with the washer part.

According to the present invention, since the collar part is formed as a single body with the washer part, it is possible to reduce the quantity of parts and time in assembling.

DETAILED DESCRIPTION OF THE INVENTION

A description is given below of a load cell attachment structure according to one embodiment of the present invention with reference to the drawings.

Figure 1:
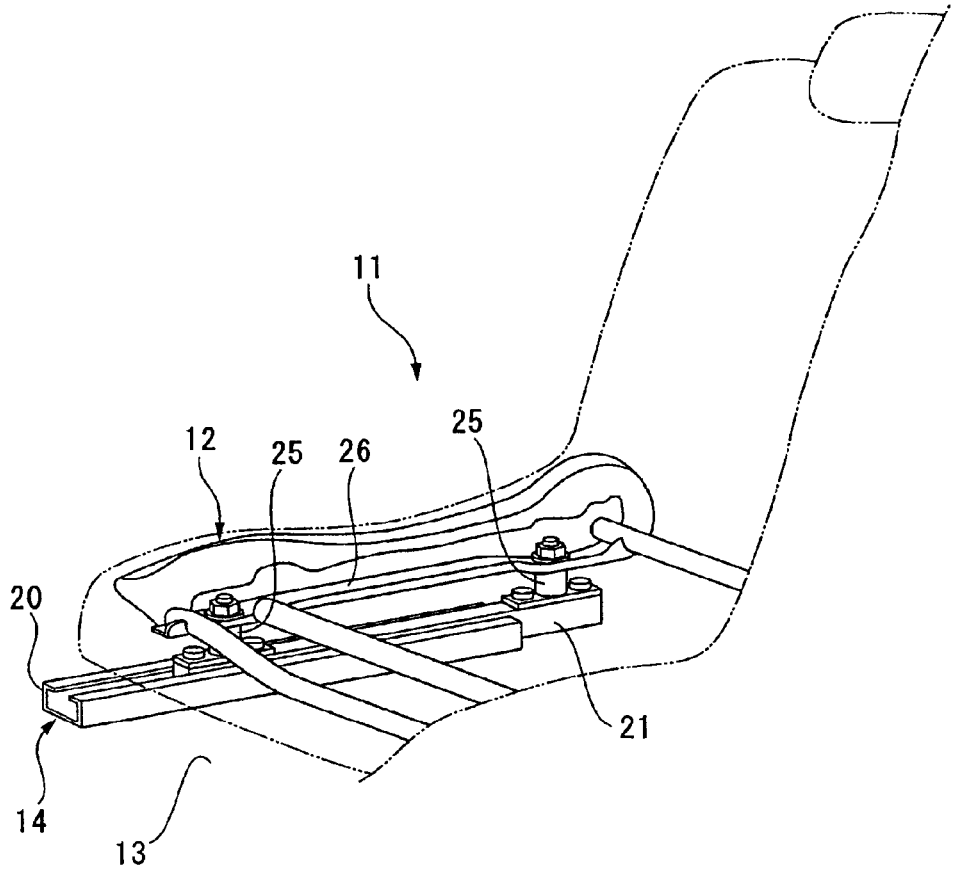
FIG. 1 is a perspective view showing the seat of a vehicle to which a load cell attachment structure according to the present invention is applied.

FIG. 1 shows the right half side of an occupant's seat 11 of a vehicle. A seat frame [11] *12* which composes a skeletal structure of the seat 11 is supported on a pair of seat rails 14 so as to be capable of sliding in the lengthwise direction of the vehicle. The seat rails 14 are spaced apart from each other in the widthwise direction of the vehicle, and are fixed on a floor panel 13 of the vehicle. Note that, only one of the pair of seat rails 14 is shown in FIG. 1.

The seat rail 14 is composed of a rail main body 20 and a slider 21. The rail main body 20 extends along the lengthwise direction of the vehicle, and is fixed on the floor panel 13. The slider 21 extends along the lengthwise direction of the vehicle, and is supported on the rail main body 20 so as to be capable of sliding in the lengthwise direction of the vehicle.

Load cells 25 which measure loads, are respectively mounted on a front end part and a rear end part of the slider 21. Attachment plates 26 spaced apart from each other in the widthwise direction of the vehicle are fixed on a floor panel 13 of the vehicle.

The pair of attachment plates 26 is disposed under the seat frame 12. One of the pair of attachment plates 26 is disposed on the right side of the seat 11, and is attached to the load cells 25 mounted on the slider 21, the other of the pair of attachment plates 26 is disposed on the left side of the seat 11, and is attached the load cells 25 mounted on that slider 21.

The load cell attachment structure of this embodiment includes a male screw 36 (first fastening part) which is formed on a load [sensing part 38] *cell main body 35* of the load cell 25, a nut 50 (second fastening part) which attaches the load cell 25 to the attachment plate 26 by engaging with the male screw 36, and a wave washer 47 (elastic body) which is disposed between the attachment plate 26 and the nut 50.

Figure 2:
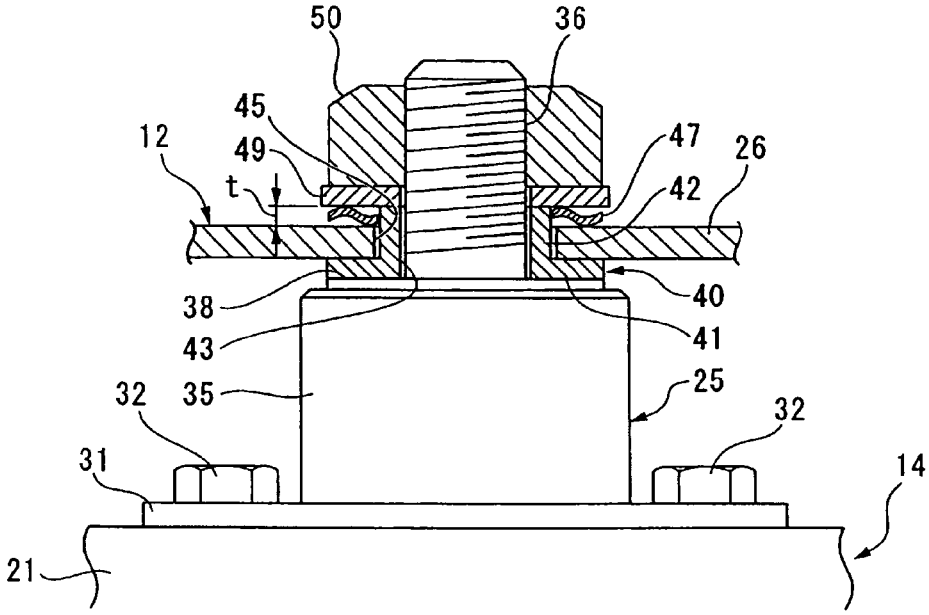
FIG. 2 is sectional view of the load cell attachment structure according to the present invention.

As shown in FIG. 2, the load cell 25 has a base plate 31 which extends in one direction. The base plate 31 is disposed along the lengthwise direction of the vehicle the left-right direction in FIG. 2. A front part and a rear part of the base plate 31 are attached to the slider 21 with bolts 32.

As in the above description, the load cell 25 is attached to the slider 21 through the base plate 31. A load cell main body 35 of the load cell 25 is fixed on the center of an upper surface of the base plate 31. The load cell main body 35 is formed as a substantially column-like shape, the direction of load of the load cell main body 35 being in the vertical direction. The male screw 36 is fixed on the center of an upper surface of the load cell main body 35 so as to be protruding upward.

The load sensing part 38 is the upper surface of the load cell main body 35 with the exception of the male screw 36. In other words, the male screw 36 is formed on the load [sensing part 38] *cell main body 35* of the load cell 25. The load cell main body 35 warps slightly when subjected to downward load from the load sensing part 38, and measures load corresponding to the amount of the warp.

A washer 40 is mounted on the load cell main body 35. The washer 40 is composed of a washer part 41 and a collar part 42. The washer part 41 is formed as a disk shape, and has a circular hole at the center thereof. The external diameter of the washer part 41 is the same as the external diameter of the load sensing part 38. The collar part 42 is formed as a cylinder shape, and the external diameter of the collar part 42 is less than the external diameter of the washer part 41. The collar part 42 is disposed on the washer part 41 so as to protrude upward from the washer part 41, and is formed as a single body with the washer part 41 so that an axis of the washer part 41 and an axis of the collar part 42 coincide. Since the axis of the washer part 41 and the axis of the collar part 42 coincide, a penetration hole 43 is formed on the washer part 40. The internal diameter of the penetration hole 43 is greater than a external diameter of the male screw 36.

The male screw 36 is inserted into the penetration hole 43, and the washer part 41 contacts the load sensing part 38, and thus the washer 40 is mounted on the load cell main body 35. In this condition, the whole of the load sensing part 38 is covered by the washer part 41. Further, since a top end of the male screw 36 of the load cell 25 protrudes upward from the washer 40, the upper surface of the washer part 41, the upper end surface of the collar part 42, and the upper surface of the load sensing part 38 are parallel with each other. It is preferable that the external diameter of the washer part 41 be the same as the external diameter of the load sensing part 38, or be greater than the external diameter of the load sensing part 38.

The male screw 36 is inserted into the collar part 42, and the collar part 42 into which the male screw 36 is inserted is inserted into an attachment hole 45 which is formed on the attachment plate 26, and thus the attachment plate 26 is mounted on the washer part 41. Note that the length of the collar part 42 in the vertical direction is greater than the thickness of the attachment plate 26, and accordingly a top end surface of the collar part 42 protrudes upward from the attachment plate 26 contacting the washer part 41.

The wave washer 47 is mounted on the attachment plate 26, which contacts the upper surface of the wave washer 47. The wave washer 47 is formed as a ring shape, and the external diameter of the wave washer 47 is greater than the external diameter of the washer part 41. The collar part 42 protruding upward from the attachment hole 45 of the attachment plate 26 is inserted into a center hole of the wave washer 47. When the wave washer 47 is not deformed, the thickness of the wave washer 47 is greater than a difference between the length of the collar part 42 in the vertical direction and the thickness of the attachment plate 26, and when the wave washer 47 is deformed, the thickness of the wave washer 47 is less than the difference between the length of the collar part 42 in the vertical direction and the thickness of the attachment plate 26. Therefore, when the wave washer 47 is mounted on the attachment plate 26 and is not deformed, a highest point of an upper surface of the wave washer 47 is positioned above the upper end surface of the collar part 42.

The washer 49 is mounted on the wave washer 47. The male screw 36 protruding upward from the penetration hole 43 of the washer 40 is inserted into a center hole of the washer 49. The internal diameter of the washer 49 is greater than the external diameter of the male screw 36, and is less than the external diameter of the collar part 42. The external diameter of the washer 49 is approximately the same as the external diameter of the wave washer 47.

The nut 50 is thread-engaged with the male screw 36. The nut is fastened at predetermined torque. Therefore, the washer 49 and the washer 40 are sandwiched to be fixed between the nut 50 and the load cell 25. That is, a lower surface of the nut 50 closely contacts an upper surface of the washer 49. Further, a lower surface of the washer 49 closely contacts the collar part 42 of the washer 40, and a lower surface of the washer part 41 of the washer 40 closely contacts an upper surface of the load sensing part 38 of the load cell main body 35. In this condition, since the washer 49 and the washer 40 are close to each other, the wave washer 47 which is sandwiched between the washer 40 and washer 49 deforms elastically. When the wave washer 47 deforms elastically, the attachment plate 26 is pushed against the washer part 41 which is positioned under the attachment plate 26 due to the elastic force of the wave washer 47.

The load cell 25 is attached to the attachment plate 26 by the nut 50 being thread-engaged with the male screw 36. Further, the whole of the load sensing part 38 is covered by the washer part 41, and the washer part 41 is sandwiched between the load sensing part 38 and the attachment plate 26. Furthermore, the collar part 42 which is thicker than the thickness of the attachment plate 26 is disposed between the washer part 41 and the nut 50. Moreover, the wave washer 47 is disposed between the attachment plate 26 and the nut 50.

As in the above description, four corners of the seat 11, that is the front part and the rear part of the pair of the seat frames 12 are supported by the seat rails 14 which are spaced apart from each other in the widthwise direction by way of the four load cells 25. Load which is added onto the seat 11 is introduced from the seat frame 12 into the load sensing part 38 through the washer part 41. The load cell main body 35 warps slightly due to being introduced load from the load sensing part 38, and generates an electrical charge corresponding to the load which is introduced through the washer part 41. The electrical charge is measured by a control section (not shown in the figures).

Based upon the load which is measured by the four load cells 25, the control section makes a decision as to whether or not a occupant is seated on the seat 11. Also, the control section makes a decision as to whether the occupant is an adult or a child. Further, based upon the decision, the control section controls the way of operating and the like of the air bag system, when a collision of the vehicle happens.

Figure 3:
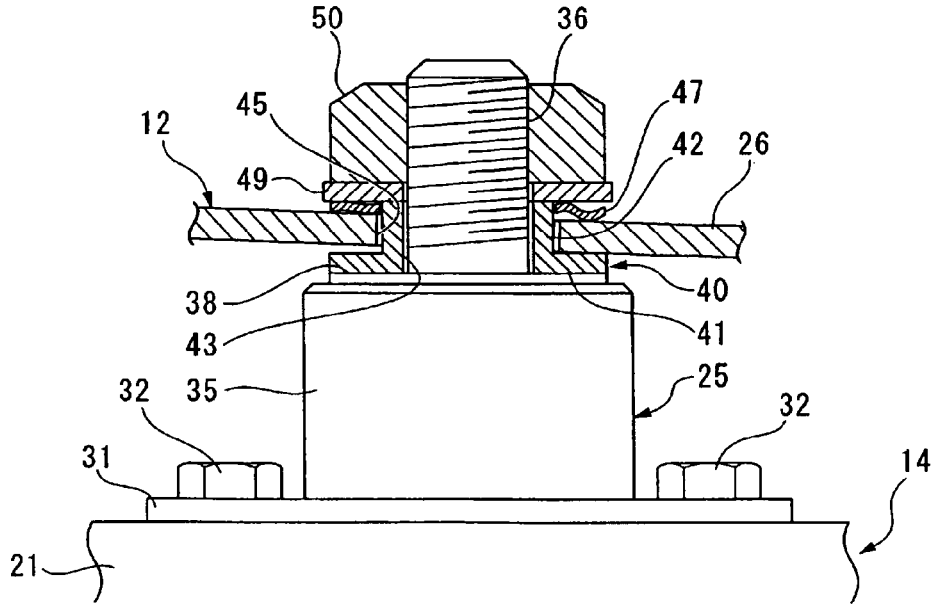
FIG. 3 is sectional view of the load cell attachment structure according to the present invention, in particular, showing a state in which the attachment plate inclines.

According to the load cell attachment structure of above described embodiment, since the wave washer 47 is disposed between the attachment plate 26 and nut 50, as shown in FIG. 3, if the attachment plate 26 warps or inclines, such warp or incline is absorbed by the deformation of the wave washer 47. Therefore, the load cell 25 does not sense an undesired load (in other words, "offset load") caused by the warp or incline of the attachment plate 26 or imperfect assembly. Further, the weight of the seat 11 and of the occupant on the seat 11 is introduced from the attachment plate 26 to the load sensing part 38 through the washer 40. As a result, it is possible to measure load which acts on the load sensing part 38 exactly.

As shown in FIG. 3, the load cell attachment structure of this embodiment includes the washer 40 which is composed of the washer part 41 and the collar part 42. The washer part 41 substantially covers the load sensing part 38, and is sandwiched between the load sensing part 38 and the attachment plate 26. The collar part 42 is disposed between the washer part 41 and the nut 50, the length of the collar part 42 in the axial direction being greater than the thickness of the attachment plate 26. In other words, the length of the collar part 42 in the axial direction is greater than the sum of the thickness of the attachment plate 26 and the minimum thickness of the wave washer 47.

Due to this, a clearance which absorbs the wrap or incline of the attachment plate 26 is appropriately formed between the nut 50 and the washer part 41 by the collar part 42. In addition, the fastening force which is introduced through the collar part 42 is dispersed on the load sensing part 38 evenly by the washer part 41. Therefore, the load cell [26] *25* does not sense an undesired load which is caused by the warp or incline of the attachment plate 26 due to a minor collision of the vehicle or the fastening force. As a result, it is possible to measure loads exactly.

In addition, the fastening force which is introduced through the collar part 42 is dispersed on the load sensing part evenly by the washer part 41. Therefore, the load cell 25 does not sense an undesired load (in other words, "drift force along the axis") which is caused by the fastening force, and dispersion of initial values of the load cell caused by difference in fastening torque can be reduced. As a result, it is possible to measure load exactly. That is, when the washer 40 is a collar only, in the total sensing range of the load sensor 25, the range defined by counting out the weight of the seat as well as drift from the fastening force becomes the range that can be used to sense the weight of the occupant. However, when the washer 40 is provided with the washer portion 41 and the collar portion 42, in the total sensing range of the load sensor 25, the range defined by counting out only the weight of the seat becomes the range that can be used to sense the weight of the occupant. Accordingly, the effective sensing range of the sensor becomes extremely wide.

Since the wave washer 47 is disposed between the attachment plate 26 and the nut 50, if the attachment plate 26 does not warp or incline, or if the attachment plate 26 warps, the wave washer 47 deforms corresponding to the warp or incline. Therefore, it is possible to reduce the backlash of the attachment plate 26 which is disposed between the washer 49 and the washer part 41.

Figure 4:
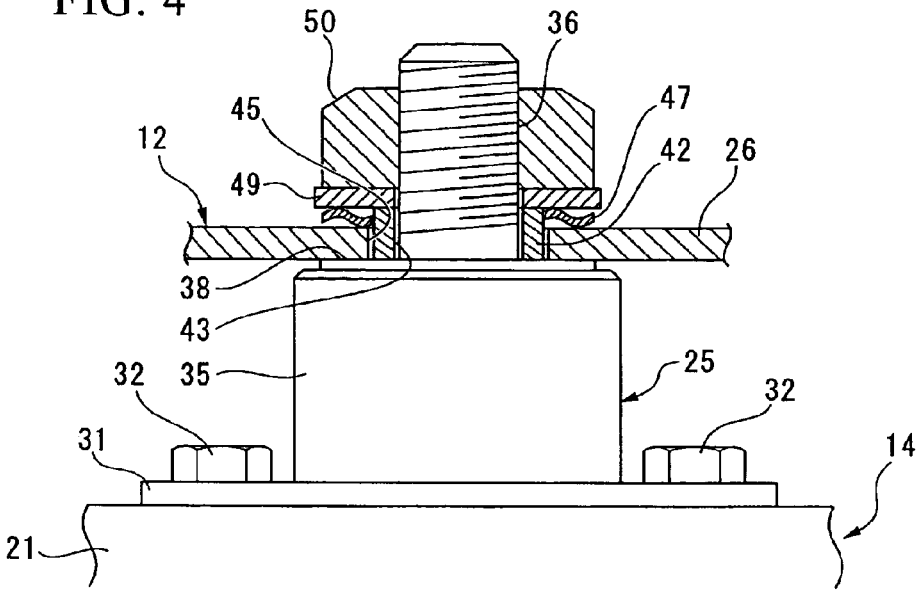
FIG. 4 is sectional view of first variant of the load cell attachment structure according to the present invention.

Since the collar part 42 is formed as a single body with the washer part 41, it is possible to reduce the quantity of parts and time in assembly. Naturally, the collar part 42 and the washer part 41 can also be separate. [Note that, if the load cell 25 can measure loads exactly without the dispersion of the fastening force over the load sensing part 38, as shown in FIG. 4, the washer 40 may include only the collar part 42 without the washer part 41.]

Figure 5:
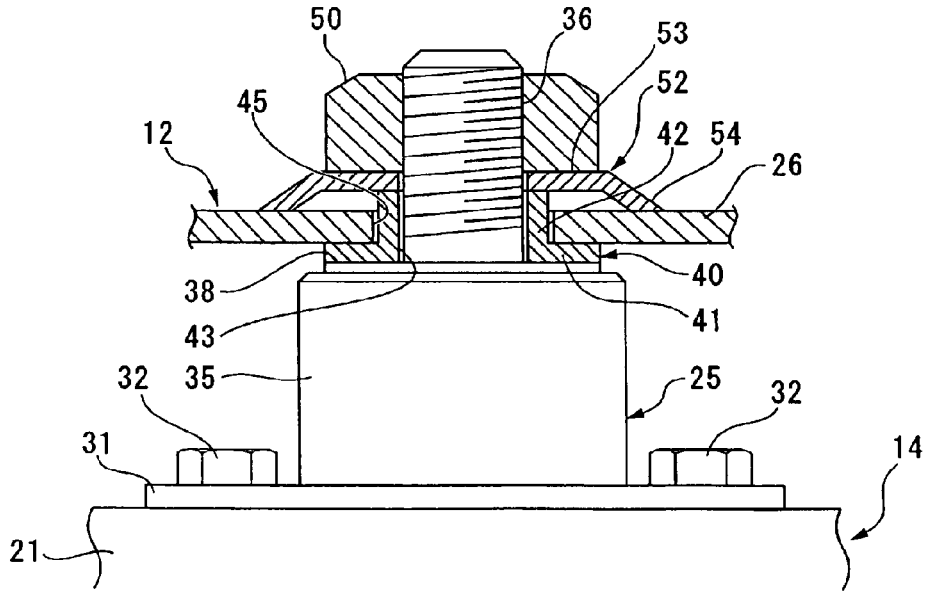
FIG. 5 is sectional view of second variant of the load cell attachment structure according to the present invention.

The load cell attachment structure of this embodiment may include another elastic body instead of the wave washer 47. For example, as shown in FIG. 5, a plate-spring shape washer 52 may be disposed between the nut 50 and the washer 41. The washer 52 is composed of a flat plate part 53 with a ring shape and a tapered part 54 which is disposed on the outside edge of the flat plate part 53. The tapered part 54 inclines with respect to the flat plate part 53. The flat plate part 53 closely contacts the lower surface of the nut 50 and the upper end surface of the collar part 42, and an outside edge of the tapered part 54 closely contacts the attachment plate 26.

Figure 6:
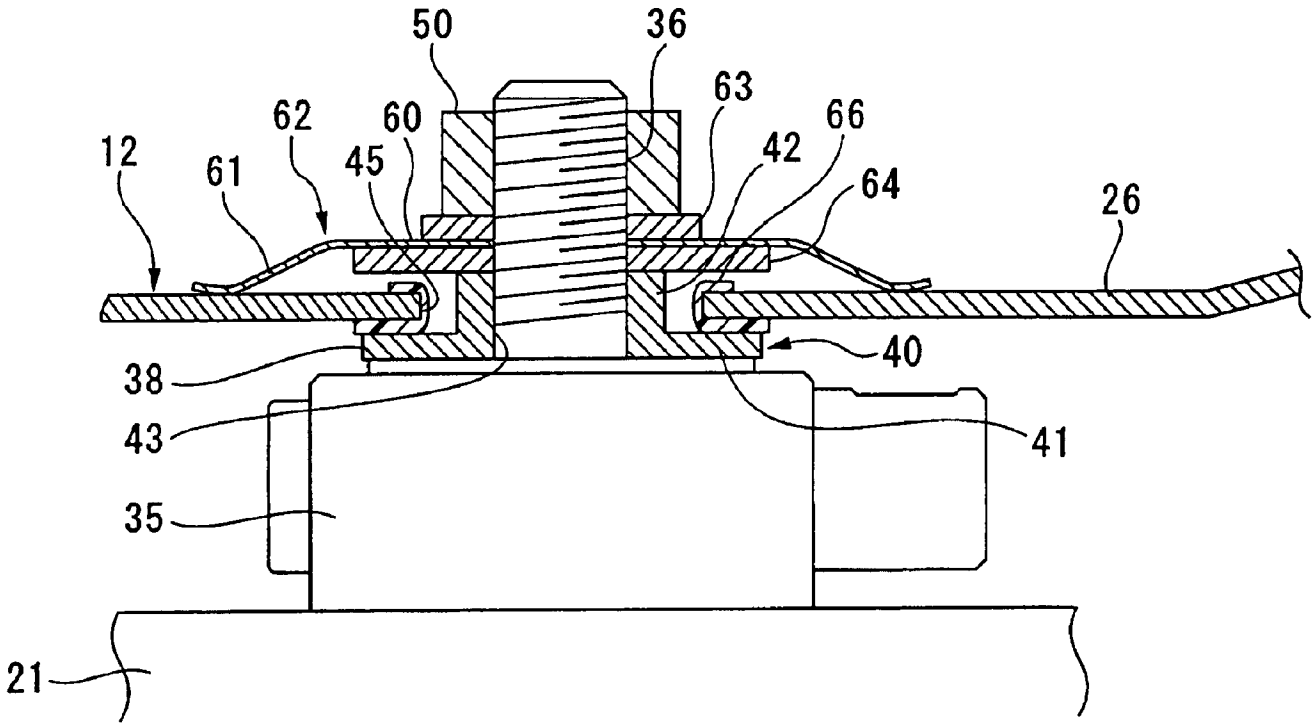
FIG. 6 is sectional view of third variant of the load cell attachment structure according to the present invention.
Figure 7:
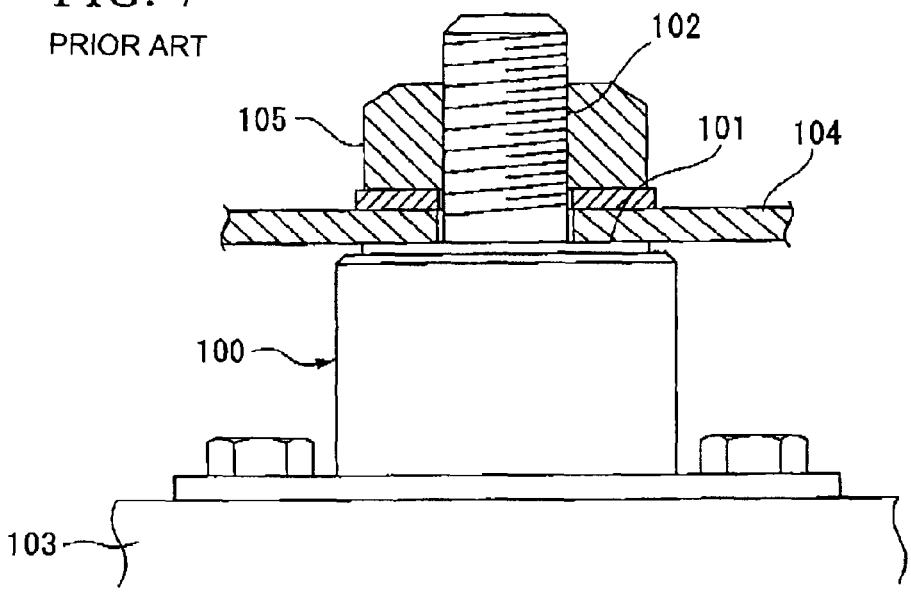
FIG. 7 PRIOR ART
FIG. 7 is sectional view of a conventional load cell attachment structure.
Figure 8:
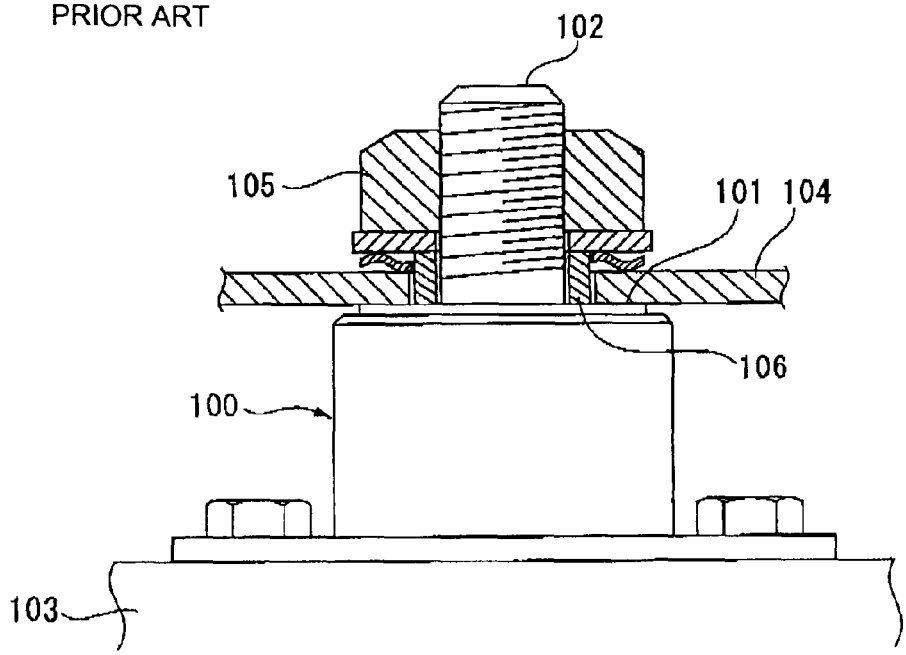
FIG. 8 PRIOR ART
FIG. 8 is sectional view of another conventional load cell attachment structure.

Further, as shown in FIG. 6, a plate-spring 62 which is sandwiched between washers 63, 64 may be disposed between the nut 50 and the washer 40. The plate-spring 62 is composed of a flat plate part 60 with a ring shape and a tapered part 61 which is disposed on the outside edge of the flat plate part 60. The tapered part 61 inclines with respect to the flat plate part 60. The washer 63 is disposed between the plate-spring 62 and the nut 50, and the washer 64 is disposed between the plate-spring 62 and the collar part 42. The external diameter of the washer 63 is less than the external diameter of the washer 64, and the external diameter of the plate-spring 62 is less than the external diameter of the washer 64. The washer 63 closely contacts the lower surface of the nut 50, and the washer 64 closely contacts the upper end surface of the collar part 42. Further, an outside edge of the taper plate part 61 closely contacts the attachment plate 26. A resinous cover 66 is disposed on an inside edge of the attachment hole 45 of the attachment plate 26. The cover 66 prevents the inside edge of the attachment hole 45 from contacting the washer 40.

In the above embodiment, the structure in which the load cell 25 is attached to the attachment plate 26 by the male screw 36 being disposed on the load sensing part 38 of the load cell 25, and the nut 50 being thread-engaged with the male screw 36, is explained. However, a structure in which the load cell 25 is attached to the attachment plate 26 by a female screw being disposed on the load sensing part 38 of the load cell 25, and a bolt being thread-engaged with the female screw, may be applied. In this structure, the bolt is inserted into the penetration hole 43, and the collar part 42 of the washer 40 is disposed between the washer part 41 and a top of the bolt. Also, the wave washer 47 is disposed between the attachment plate 26 and the top of the bolt.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A load cell attachment structure for attaching a load cell to an attachment plate, *the load cell including a main body and a load sensing part, the load cell attachment structure* comprising:

a first fastening part which is formed on [a load sensing part] *the main body* of the load cell;

a second fastening part which attaches the load cell to the attachment plate by engaging with the first fastening part;

an elastic body which is disposed between the attachment plate and the second fastening part; and a washer part which entirely covers the load sensing part, and is disposed between the attachment plate and the load sensing part.

2. A load cell attachment structure according to claim 1, further comprising:

a collar part which is disposed between the washer part and the second fastening part, wherein a length of the collar part along an axis thereof is longer than a thickness of the attachment plate.

3. A load cell attachment structure according to claim 2, wherein the first fastening part comprises a male screw, the second fastening part comprises a nut, the elastic body is disposed between the attachment plate and the nut, and the collar part is disposed between the washer part and the nut.

4. A load cell attachment structure according to claim 2, wherein the collar part is formed as a single body with the washer part.

5. A load cell attachment structure for attaching a load cell to an attachment plate, *the load cell including a main body and a load sensing part, the load cell attachment structure* comprising:

a first fastening part which is formed on [a load sensing part] *the main body* of the load cell;

a second fastening part which attaches the load cell to the attachment plate by engaging with the first fastening part;

a washer part which entirely covers the load sensing part, and is disposed between the load sensing part and the attachment plate; and a collar part which is disposed between the washer part and the second fastening part, wherein a length of the collar part along an axis thereof is longer than a thickness of the attachment plate.

6. A load cell attachment structure according to claim 5, wherein the first fastening part comprises a male screw, the second fastening part comprises a nut, and the collar part is disposed between the washer part and the nut.

7. A load cell attachment structure according to claim 5, wherein the collar part is formed as a single body with the washer part.

8. A load cell attachment structure for attaching a load cell to an attachment plate, *the load cell including a main body and a load sensing part, the load cell attachment structure* comprising:

a male screw which is formed on [a load sensing part] *the main body* of the load cell and which is inserted into an attachment hole formed in the attachment plate;

a nut which attaches the load cell to the attachment plate by engaging with the male screw;

an elastic body which is disposed between the attachment plate and the nut fastened on the male screw; and a washer having a washer part and a collar part and which is disposed between the load sensing part and the attachment plate, in which the washer part covers all of the load sensing part and contacts the load sensing part, and the collar part is disposed between the washer part and the nut, wherein the male screw is inserted into the collar part, the collar part is inserted into the attachment hole, the length of the collar part along an axis thereof is longer than a thickness of the attachment plate to have a space between the nut and the attachment plate, and the elastic body having a thickness greater than the space is disposed between the attachment plate and the nut, and the nut is engaged with the male screw until the nut contacts the collar part.

9. A load cell attachment structure for attaching a load cell to an attachment plate, *the load cell including a main body and a load sensing part, the load cell attachment structure* comprising:

a male screw which is formed on [a load sensing part] *the main body* of the load cell and which is inserted into an attachment hole formed in the attachment plate;

a nut which attaches the load cell to the attachment plate by engaging with the male screw;

a plate-spring which is composed of a flat plate part and a tapered part disposed on the outside edge of the flat plate part and which is disposed between the attachment plate and the nut fastened on the male screw to push the attachment plate to the load sensing part; and[,]

a washer having a washer part and a collar part and which is disposed between the load sensing part and the attachment plate, in which the washer part contacts the load sensing part, and the collar part is disposed between the washer part and the nut;

wherein the flat plate part of the plate spring is disposed between the collar part and the nut.

10. The load cell attachment structure according to claim 9, wherein an elastic cover is disposed on an edge of the attachment hole.

11. The load cell attachment structure according to claim 10, wherein a space is formed between the elastic cover and the collar part.

12. The load cell attachment structure of claim 10, wherein the elastic cover is disposed between the attachment plate and the washer part.

13. The load cell attachment structure according to claim 9, wherein a second washer is disposed between the flat plate part and the collar part.

14. The load cell attachment structure according to claim 13, wherein a third washer is disposed between the nut and the flat plate part, and an outer diameter of the third washer is larger than that of the second washer.

*15. The load cell attachment structure according to claim 2, wherein the elastic body is arranged at a periphery of the collar part.*

*16. The load cell attachment structure according to claim 4, wherein the elastic body is arranged at a periphery of the collar part.*

*17. The load cell attachment structure according to claim 1, wherein the washer part contacts the load sensing part.*

*18. The load cell attachment structure according to claim 1, wherein an outer edge of the elastic body is farther than a periphery of the main body of the load cell from the first fastening part arranged at a center of the main body.*

*19. The load cell attachment structure according to claim 1, wherein the washer part is larger in diameter than the load sensing part.*

*20. The load cell attachment structure according to claim 1, wherein an outer edge of the elastic body is farther than a periphery of the main body of the load cell from the male screw arranged at the center of the main body.*

*21. The load cell attachment structure according to claim 7, wherein the load cell warps when load downwardly acts on the load sensing part, and thereby the load acting on the load sensing part is measured by the load cell.*

*22. The load cell attachment structure according to claim 7, further comprising an elastic body which is disposed between the washer part and the second fastening part.*

*23. The load cell attachment structure according to claim 22, wherein the elastic body includes an inclination part.*

*24. The load cell attachment structure according to claim 5, wherein the washer part contacts the load sensing part.*

*25. The load cell attachment structure according to claim 5, wherein the load cell warps when a load downwardly acts on the load sensing part, and thereby the load acting on the load sensing part is measured by the load cell.*

*26. The load cell attachment structure according to claim 5, further comprising an elastic body which is disposed between the washer part and the second fastening part.*

*27. The load cell attachment structure according to claim 26, wherein the elastic body includes an inclination part.*

*28. The load cell attachment structure according to claim 26, wherein a second washer is disposed between the collar part and a nut included in the second fastening part.*

*29. The load cell attachment structure according to claim 26, wherein the elastic body includes a bending part.*

*30. The load cell attachment structure according to claim 26, wherein an end of the elastic body close to the second fastening part contacts a second washer.*

*31. The load cell attachment structure according to claim 26, wherein the attachment plate includes an attachment hole to which the first fastening part is inserted, and*

*a cover is disposed between a hole portion and the collar part.*

*32. The load cell attachment structure according to claim 31, wherein the cover prevents the collar part from contacting an attachment hole of an attachment plate.*

*33. The load cell attachment structure according to claim 31, wherein the cover is an independent member from the elastic body.*

*34. The load cell attachment structure according to claim 31, wherein the cover comprises an insertion portion to be inserted to the attachment hole, and an extension part outwardly-extending in a radial direction from the insertion portion.*

*35. The load cell attachment structure according to claim 31, wherein the elastic body includes a bending part.*

*36. The load cell attachment structure according to claim 5, wherein a second washer is disposed between the collar part and a nut included in the second fastening part.*

*37. The load cell attachment structure according to claim 5, further comprising an elastic body which is disposed between the attachment plate and the second fastening part, wherein the elastic body includes a bending part.*

*38. The load cell attachment structure according to claim 5, wherein the washer part is larger in diameter than the load sensing part.*

*39. The load cell attachment structure according to claim 5, further comprising an elastic body which is disposed between the attachment plate and the second fastening part, wherein an end of the elastic body close to the second fastening part contacts a second washer.*

*40. The load cell attachment structure according to claim 5, further comprising an elastic body which is disposed between the attachment plate and the second fastening part, wherein the elastic body is arranged at a periphery of the collar part.*

*41. The load cell attachment structure according to claim 5, further comprising an elastic body which is disposed between the attachment plate and the second fastening part, wherein an outer edge of the elastic body is farther than a periphery of the main body of the load cell from the male screw arranged at the center of the main body.*

*42. The load cell attachment structure according to claim 5, wherein the attachment plate includes an attachment hole to which the first fastening part is inserted, and*

*a cover is disposed between a hole portion and the collar part.*

*43. The load cell attachment structure according to claim 42, wherein the cover prevents the collar part from contacting an attachment hole of an attachment plate.*

*44. The load cell attachment structure according to claim 8, wherein the washer part contacts the load sensing part.*

*45. The load cell attachment structure according to claim 8, wherein an outer edge of the elastic body is farther than a periphery of the main body of the load cell from the male screw arranged at a center of the main body.*

*46. The load cell attachment structure according to claim 8, wherein the elastic body is arranged at a periphery of the collar part.*

*47. The load cell attachment structure according to claim 8, wherein the washer part is larger in diameter than the load sensing part.*

*48. A load cell attachment structure for attaching a load cell to an attachment plate, the load cell including a main body and a load sensing part, the load cell attachment structure comprising:*

*a first fastening part which is formed on the main body of the load cell;*

*a second fastening part which attaches the load cell to the attachment plate by engaging with the first fastening part;*

*a washer part which entirely covers the load sensing part, and is disposed between the load sensing part and the attachment plate;*

*a collar part which is disposed between the washer part and the second fastening part; and*

*an elastic body which is disposed between the washer part and the second fastening part, wherein*

*the elastic body is arranged at a periphery of the collar part, and*

*a length of the collar part along an axis thereof is longer than a thickness of the attachment plate.*

*49. The load cell attachment structure according to claim 48, wherein the elastic body includes an inclination part.*

*50. The load cell attachment structure according to claim 48, wherein a second washer is disposed between the collar part and a nut included in the second fastening part.*

*51. The load cell attachment structure according to claim 48, wherein the elastic body includes a bending part.*

* * * * *